(12) United States Patent
Kusaka

(10) Patent No.: US 7,972,636 B2
(45) Date of Patent: Jul. 5, 2011

(54) BEVERAGE AND MEDICAMENT CONTAINING BAMBOO EXTRACT AS A MAIN INGREDIENT

(76) Inventor: Hidemoto Kusaka, Saitama (JP)

( * ) Notice: Subject to any disclaimer, the term of this patent is extended or adjusted under 35 U.S.C. 154(b) by 587 days.

(21) Appl. No.: 11/960,409

(22) Filed: Dec. 19, 2007

(65) Prior Publication Data

US 2008/0107760 A1     May 8, 2008

Related U.S. Application Data

(63) Continuation-in-part of application No. 10/589,452, filed as application No. PCT/JP2004/002161 on Feb. 25, 2004, now abandoned.

(51) Int. Cl.
*A61K 36/899* (2006.01)
*A61K 36/81* (2006.01)
*A61K 36/33* (2006.01)

(52) U.S. Cl. ............ 424/750; 424/760; 424/767

(58) Field of Classification Search .............. None
See application file for complete search history.

(56) References Cited

U.S. PATENT DOCUMENTS 5,976,644 A * 11/1999 Sanaee et al. ............ 428/17

FOREIGN PATENT DOCUMENTS

| CN | 1100609 A | | 3/1995 |
|---|---|---|---|
| CN | 1115617 A | | 1/1996 |
| CN | 1331932 A | | 1/2002 |
| JP | 57-39753 A | | 3/1982 |
| JP | 7-33635 A | | 2/1995 |
| JP | 8-291057 A | | 11/1996 |
| JP | 63290825 A | | 11/1998 |
| JP | 11-27965 A | | 10/1999 |
| JP | 2003-60487 A | | 2/2000 |
| JP | 2000-70964 A3 | | 3/2000 |
| JP | 2003-317463 A | | 11/2000 |
| JP | 2001095521 A | * | 4/2001 |
| JP | 2003-12537 A | | 1/2003 |
| JP | 2003009803 A | * | 1/2003 |
| JP | 2003-112774 A | | 4/2003 |
| JP | 2004-337151 A | | 2/2004 |
| WO | 01/39725 A | | 6/2001 |

OTHER PUBLICATIONS

Akahisha, T., et al., "Skin external preparation for use as antiallergic agent for preventing atopic dermatitis, allergic symptoms, itching, pruritus, athelete's foot and miliaria, contains bamboo extract," DATABASE WPI (Jan. 1, 1900).
Chun Hu, et al., "Evaluation of Antioxidant and Prooxidant Activities of Bamboo Phyllostachys Nigra Var. Henonis Leaf Extract into Vitro," Journal of Agricultural and Food Chemistry, American Chemical Society, vol. 48, No. 8, pp. 3170-3176 (Jul. 14, 2000).
"Production of Antioxidant property-natural drinking water, for inpatients, involves blending Mousou-bamboo extract with water, obtained by filtering mountain stream water," DERWENT (Jan. 1, 1900).
Ando, H., et al., "Growth Inhibition Effect on some Cancer Cell Lines by Hot Compressed Water Extractives of Moso Bamboo (Pyllostachys pubescens)," Journal—Japan Wood Resaerch Society, vol. 49; Part 5, pp. 371-376 (2003).
Adachi, T., et al., "Benikamikirifurasu oyobi Mosochiku Seibun no Ko-Allergy Kassei," Hesei 14 Nendo Nihon Univesity Riko Gakubu Gakujutsu Koen Ronbunshu, 46th, pp. 1278-1279 (2002).
Nishina, a., "Mosochiku Chushutsbutsu no Kokin Kassei," Food Chemicals, vol. 6, No. 5, pp. 36, 39 (1998).
Yasuda, S., et al., "Dietary Effects of Gingko Biloba and Bamboo Extract Powders on Lipid Metabolism and Immune Function of Sprague Dawley Rats," Science Bulletin Faculty of Agriculture Kyushu University, vol. 57; Part 1, pp. 17-26 (2002).
Tanaka, N., "Constituents of Bamboos and Bamboo Grasses," Journal of the Pharmaceutical Society of Japan, vol. 118, No. 8, pp. 332-337 (1998).

* cited by examiner

*Primary Examiner* — Christopher R Tate
*Assistant Examiner* — Deborah A. Davis
(74) *Attorney, Agent, or Firm* — Ladas & Parry, LLP

(57) ABSTRACT

The present invention relates to a beverage containing bamboo extract as a main ingredient, for details, a beverage containing bamboo extract as the main ingredient, which is useful for amelioration of diabetes, cancer, life-style related diseases or the like. A beverage characterized in containing, as the main ingredient, bamboo extract obtained through the process comprising the steps by immersing bamboo in water and extracting the bamboo extract with heating the water to 95° C. or higher and maintaining the temperature for a period of 2 hr 45 min to 3 hr 15 min.

13 Claims, 1 Drawing Sheet

BEVERAGE AND MEDICAMENT CONTAINING BAMBOO EXTRACT AS A MAIN INGREDIENT

CROSS-REFERENCE TO RELATED APPLICATIONS

This application is a continuation-in-part of application Ser. No. 10/589,452, filed on Aug. 11, 2006, now abandoned, which is the U.S. National Stage of International Application No. PCT/JP2004/002161, filed on Feb. 25, 2004, the disclosure of which is incorporated herein by reference.

TECHNICAL FIELD

The present invention relates to a beverage containing bamboo extract as a main ingredient, for details, a beverage containing bamboo extract as a main ingredient which is useful for amelioration of diabetes, cancer, life-style related diseases or the like.

BACKGROUND ART

It has been hitherto known that the six major nutrients (water, carbohydrate, protein, lipid, mineral, and vitamin) are necessary to maintain human health.

However, a modern food life in Japan, which is called "westernization of food life", tends to decreases the amount of ingested cereals, vegetables, seaweeds, beans, and fishes and the like because the food life is largely composed of meats. This causes a problem that nutrients from vegetables or the like are deficient.

To solve the above problem, supplements are prevailed and ingested by many people because they can easily make up the lack of nutrients. For example, it is proposed to take supplements as a simple means to make up the lack of nutrients missing in the modern food life in the patent literatures-1 and -2. Thus, the supplements are important in the sense of making up insufficient nutrients.

However, taking supplements can cause some problems. One of the problems is an excess ingesting of nutrients obtained from the supplements according to the idea that the supplements are good for health. Another is that a sense of reassurance from taking the supplements every day results in breaking the food life much more.

In addition to such food life, irregular life-style, lack of exercise, stress and the like cause many diseases such as diabetes, cancer, allergies, life-style related diseases and so on. The above has become a serious social problem.

DISCLOSURE OF THE INVENTION

Figure 1:
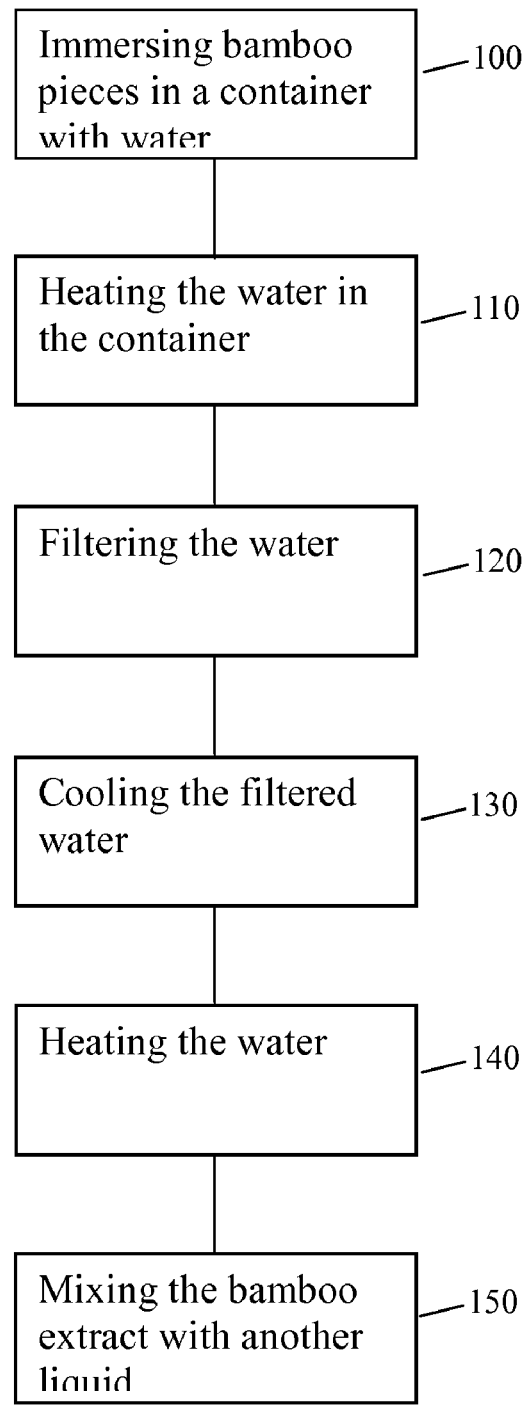
FIG. 1 depicts an exemplary embodiment of obtaining bamboo extract according to the present application.

The present invention is, considering the above-mentioned actual circumstances, a beverage containing bamboo extract as the main ingredient. An object of the present invention is amelioration of diseases, including diabetes, complications of diabetes, cancer, hepatic dysfunction, stiff shoulder, atopy, allergy, pollinosis, life-style related diseases, climacteric disorders, recovery from fatigue, recovery of vitality, rheumatism, neuralgia, insomnia, constipation, diarrhea, body odor, chloasma, freckle, wrinkles, dandruff, itch of tinea pedis, chapped skin, accelerating hair growth, frozen shoulder, and peritendinitis by drinking a beverage containing bamboo extract as the main ingredient or applying it to affected parts.

The above-mentioned object of the present invention is achieved effectively by a beverage containing, as the main ingredient, bamboo extract obtained through the process comprising the steps of immersing bamboo in water and extracting the bamboo extract with heating the water to 95° C. or higher and maintaining the temperature for a period of 2 hr 45 min to 3 hr 15 min.

In addition, the above-mentioned object of the present invention is achieved more effectively by a beverage containing, as the main ingredient, bamboo extract obtained through the process comprising the steps of immersing bamboo in water and extracting the bamboo extract with heating the water to 95° C. or higher and maintaining the temperature for a period of 2 hr 45 min to 3 hr 15 min wherein the beverage is mixed with herbs. Alternatively the above-mentioned object of the present invention is achieved more effectively by a beverage containing, as the main ingredient, bamboo extract obtained through the process comprising the steps of immersing bamboo in water and extracting the bamboo extracts with heating the water to 95° C. or higher and maintaining the temperature for a period of 2 hr 45 min to 3 hr 15 min wherein the beverage is mixed with spices.

Furthermore, the above-mentioned object of the present invention is achieved effectively by a beverage containing, as the main ingredient, bamboo extract obtained through the process comprising the steps of immersing bamboo in water and extracting the bamboo extract with heating the water to 95° C. or higher and maintaining the temperature for a period of 2 hr 45 min to 3 hr 15 min wherein the beverage is mixed with sodium hyaluronate.

The above-mentioned object of the present invention is achieved by a beverage containing, as the main ingredient, Phyllostachys heterocyclabamboo extract.

BEST MODE FOR CARRYING OUT THE INVENTION

A beverage containing bamboo extract as the main ingredient of the present invention may contain the bamboo extract from *Phyllostachys bambusoides, Pleioblastus hindsii* or the like, more preferably *Phyllostachys heterocycla*.

Preparing process to obtain the beverage containing bamboo extract as the main ingredient of the present invention is described below.

First, bamboo is cut to have the same length for being adjusted to the size of a container and further split longitudinally 3 to 5 [cm] wide. The split bamboo pieces are bundled by 20 to 30 pieces. The bamboo pieces are immersed in water in a container. The water is heated to 95° C. or higher and the temperature is maintained for a period of 2 hr 45 min to 3 hr 15 min. Subsequently, a beverage containing bamboo extract as the main ingredient are obtained by taking the bamboo pieces out of the water with maintaining the temperature of 95° C. or higher.

The bamboo extract may be mixed with herbs depending on the necessity by adding them in the steps of immersing bamboo in water and heating the water to 95° C. or higher. Herbs include, but are not limited to, rosemary, marjoram, leaf of red perilla, fennel, thyme, spearmint, lemon grass and the like. Another herb or a plurality of herbs may be used. Amount of the herbs mixed into the bamboo extract is not limited, but preferably about 2% in the beverage containing bamboo extract as the main ingredient of the present invention.

In addition, the bamboo extract may be mixed with spices by adding them in the steps of immersing the bamboo in water and heating the water to 95° C. or higher. Spices include, but are not limited to, stems of red perilla, honey, royal jelly and the like. Another spice or a plurality of spices may be used. Amount of spices mixed into the bamboo extract is not limited, but preferably about 10% in the beverage containing bamboo extract as the main ingredient of the present invention. The bamboo extract may be mixed with both herbs and spices.

The beverage containing bamboo extract as the main ingredient extracted from the above method contains minerals such as calcium, potassium, zinc, magnesium, iron, phosphorus and the like and vitamins such as vitamin B1, vitamin B2, vitamin B6, niacin, carotene and, especially, has an abundance of calcium, magnesium, zinc, and potassium.

Calcium acts to maintain the strength of bones and teeth, blood coagulation, activity of muscles, neurotransmission, regulation of the heartbeat, and the like. It is known that a calcium deficiency causes numbness of limbs, muscle convulsions, heart palpitations, insomnia, osteoporosis, and edema and the like.

Magnesium is a mineral needed for metabolism of carbohydrates, lipids, proteins, calcium, phosphorus and potassium. It is known that a magnesium deficiency causes myalgia, emotional instability, hypotension, nervous erethism, hysteria and the like.

Zinc is a mineral needed for absorption and activity of the B-complex vitamins. It is known that a zinc deficiency causes a decline in learning ability, edema, fatigue, high cholesterol, decrease in appetite, dysgeusia, bad blood circulation, delay in recovery from injury, white spots on nails and the like.

Potassium is a mineral needed for maintaining osmotic pressure in cells by attracting the water with sodium and transporting substances inside and outside cells. It is known that a potassium deficiency causes hypertension, strokes, lethargy, arrhythmia, cardiac failure, anorexia, constipation, dysuria, weakening muscles, edema and the like.

The bamboo can be used preferably to ameliorate diseases such as diabetes, complications of diabetes, cancer, hepatic dysfunction, stiff shoulder, atopy, allergies, pollinosis, life-style related diseases, climacteric disorders, recovery from fatigue, recovery of vitality, rheumatism, neuralgia, insomnia, constipation, diarrhea, body odor, chloasma, freckles, wrinkles, dandruff, itch from tinea pedis, chapped skin, accelerating hair growth, frozen shoulder, peritendinitis and the like because the bamboo is a natural ingredient and can be ingested safely.

Diabetes is one of the life-style related diseases and mainly caused by obesity, high fat, lack of exercise and the like. The diabetes develops when the secretory ability of insulin decreases or insulin does not fulfill its function.

The diabetes is generally treated by diet therapy. In the diet therapy, diabetic patients must cut down on ingesting food to decrease the amount of ingested calorie. Consequently, the amounts of ingested minerals and vitamins tend to decrease necessarily. In addition, magnesium and zinc especially are deficient in diabetic patients because sugars, magnesium, and zinc in diabetic patients are simultaneously discharged into the urine. Magnesium cannot help the activity of B-complex vitamins and coenzymes it magnesium is deficient in a human body. Since an enzyme operating to ATPs (adenosine triphosphate) cannot be helped in particular, the magnesium deficiency in diabetic patients makes them more susceptible to complications of diabetes such as arteriosclerosis, angina pectoris, cardiac infarction, retinopathy, cerebral infarction and the like.

Furthermore, functions of T-lymphocytes, especially SOD (superoxide dismutase), decline when zinc is deficient in a human body. The zinc deficiency in diabetic patients makes them more susceptible to complications of diabetes such as infectious disease, ulcer, retinal detachment, macular degeneration, anosmia, ageusia and the like.

Consequently, the diabetic patients can effectively ingest magnesium and zinc by drinking the beverage containing bamboo extract as the main ingredient of the present invention, resulting in amelioration and prevention of complications of diabetes.

In addition, the reasons are not clear why drinking the beverage containing bamboo extract as the main ingredient of the present invention causes decreases in the blood glucose level and secretion of insulin but it may be considered as below.

Calcium are ionized into calcium ions in a human body. Secretory granules containing insulin are transported out of cells when the calcium ion concentration increases in the cells. Since the beverage containing bamboo extract as the main ingredient of the present invention contains much calcium as mentioned above, it is considered that the calcium ion concentration increases in the body and secretory granules containing insulin are transported out of the cells.

The reason can be explained as below why the beverage containing bamboo extract as the main ingredient of the present invention can ameliorate not only the diabetes but also cancer.

First, when cancer cells develop, NK (natural killer) cells act before the cells of the immune system act. NK cells recognize and kill infected or malignant cells (cancer cells) by directly contacting other cells in the body.

Second, macrophages having recognized cancer cells secrete interleukin-1. Furthermore, they stimulate helper/inducer T-cells to secrete interleukin-2. Remains phagocytosed by macrophages are attached by major histocompatibility complexes MHC-1 and MHC-2, and are ferried to the cell surface. The remains attached by MHC-1 contact with $T_8$-lymphocyte when they come close to the cell surface. $T_8$-lymphocytes activate and proliferate cytotoxic T-cells, which are the killer cells. $T_8$-lymphocytes produce simultaneously suppressor T-cells, which regulate to produce antibodies. Cytotoxic T-cells are able to phagocytose cancer cells in an early stage, and plasma cells are produced by suppressor T-cells. The plasma cells are stimulated by the interleukin-2 and produces immunoglobulin IgG. Immunoglobulin IgG dissolves membranes of cancer cells and they are vanished.

However, the decline of immunological function by stress or irregular life and the like causes the activity of NK-cells retarded and accelerates the cancer cell growing rate. Since some disorders in T-lymphocytes result from the declined ability of the entire immunological function, the plasma cells and immunoglobulin IgG cannot be produced. The cancer cells are unable to be vanished and further begin to proliferate if the immunoglobulin IgG are not produced. Since if the cancer cells form a membrane in proliferating, leukocytes cannot enter them to make them vanished, they further proliferate and impair the functions of the internal organs around them.

The beverage containing bamboo extract as the main ingredient of the present invention contains a growth hormone, cytokinin, which is present only in plants. Cytokinin is a generic term for the substance that has the same function as kinetin (6-furfurylaminopurine), which is a biologically active substance isolated from catabolites of DNA (deoxyribonucleic acid) as a substance promoting cell growth in plant tissue cultures. Many cytokinins are known such as purine derivatives, urea derivatives, azapurine derivatives, and deazapurine derivatives of kinetin. Cytokinin has a common function that is a growth-regulating activity in each organ of plants. The cytokinin acts as interleukin-1 or -2 and stimulates the plasma cells to secrete immunoglobulin IgG, when it enters the body of cancer patients. The immunoglobulin IgG lyses the membrane with which a cancer cell is covered. Leukocytes are able to invade and vanish the cancer cell as the membrane disappears.

In addition, the beverage containing bamboo extract as the main ingredient of the present invention contains abscisic acid, which has a high reducing power. Decreased functions of organs caused by the presence of cancer cells are recovered by abscisic acid.

The beverage containing bamboo extract as the main ingredient of the present invention is able to ameliorate diseases besides diabetes and cancer such as allergy, atopy, and pollinosis.

The immunoglobulin IgE receptor is present on an adiposis cell. If immunoglobulin IgE binds to the IgE receptor prior to IgE antibody, an allergic reaction does not occur. However if IgE antibody binds to IgE receptor prior to immunoglobulin IgE, an antigen-antibody reaction occurs and immunoglobulin IgE reacts to allergens such as histamine and heparin and the like, resulting in an allergic reaction.

The beverage containing bamboo extract as the main ingredient of the present invention contains cytokinin as mentioned above. The cytokinin replenishes interleukin-1 or -2 and binds to the IgE receptor prior to IgE antibody, resulting in the fact that the allergy or atopy reaction does not occur.

The beverage containing bamboo extract as the main ingredient of the present invention is able to ameliorate diseases caused by aging or abnormality of hormone balance such as climacteric disorder, recovery from fatigue, recovery of vitality, neuralgia, chloasma, freckles, wrinkles, accelerating hair growth, and the like besides diabetes, cancer, allergies, and atopy.

It is considered that cytokinin in the beverage of the present invention is able to ameliorate disadvantageous actions caused by aging of cells by delaying the onset of morphological alterations associated with aging as mentioned above.

The cause would be clarifies in the further research why the beverage containing bamboo extract as the main ingredient of the present invention has surprising effects to ameliorate stiff shoulder, frozen shoulder, peritendinitis, rheumatism, constipation, diarrhea, chapped skin, body odor, dandruff, itch of tinea pedis and so on besides the diseases mentioned above. However, the cause is considered that the blood flow is notably ameliorated after ingesting the beverage containing bamboo extract as the main ingredient of the present invention and cytokinin stimulates plasma cells to secrete immunoglobulin, resulting in the improvement in immunity.

The beverage containing bamboo extract as the main ingredient of the present invention ameliorates various diseases not only by drinking it but also applying it to the affected parts. For example, stiff shoulder is able to be ameliorated by directly applying the beverage containing bamboo extract as the main ingredient of the present invention to the shoulder (affected part). Furthermore, the beverage containing bamboo extract as the main ingredient of the present invention can make it easier to apply it by being mixed with aloe-containing cream.

In addition, a satiety center is stimulated by applying the beverage containing bamboo extract as the main ingredient of the present invention to the upper surface of stomach, and the patients with insomnia can sleep spontaneously and deeply (amelioration of insomnia).

Furthermore, hair growth effect can be improved more by mixing the beverage containing bamboo extract as the main ingredient of the present invention with aloe and capsaicin.

We prepared a medicament that mixed the beverage containing bamboo extract as the main ingredient of the present invention with sodium hyaluronate, which has a moisturizing effect. The medicament can ameliorate effectively stiff shoulder, frozen shoulder, diabetes and peritendinitis by applying it. In the above-mentioned medicament, it is preferable that the component part comprising the bamboo extract of the present invention for a beverage is contained at 15%-25% of the whole medicament, with sodium hyaluronate being at 0.2%-2%. One or more other components such as preservative, alcohol, and the like can be contained alone or in combination thereof.

Examples of the beverage containing bamboo extract as the main ingredient of the present invention are concretely explained below, but the present invention is not limited to these examples.

EXAMPLE

Example-1

We prepared a beverage containing bamboo extract as the main ingredient of the present invention and examined patients who had drunk it for the purpose of testing it. The examination was conducted by observing the patients' blood glucose level before and after drinking the beverage. The tested patients were diabetic patients 1-5 (four males, one female, age range 42-62), asked to drink the beverage for one week. The patients 1, 4, and 5 drank 200 [ml] of the beverage after getting up every morning. The patients 2 and 3 each drank 100 [ml] of the beverage on an empty stomach three times per day.

Table 1 shows the patients' blood glucose level before drinking the beverage, their blood glucose level after three days of drinking it, and the condition of drinking it.

TABLE 1

| PATIENT | SEX | AGE | Blood glucose level before drinking the beverage | Blood glucose level after drinking the beverage | Condition of drinking the beverage |
|---|---|---|---|---|---|
| Patient 1 | female | 54 | 325 | 160 | Drinking 200 [ml] of the beverage after getting up every morning |
| Patient 2 | male | 42 | 430 | 170 | Drinking 100 [ml] of the beverage on an empty stomach three times per day |

TABLE 1-continued

| PATIENT | SEX | AGE | Blood glucose level before drinking the beverage | Blood glucose level after drinking the beverage | Condition of drinking the beverage |
|---|---|---|---|---|---|
| Patient 3 | male | 47 | 380 | 165 | Drinking 100 [ml] of the beverage on an empty stomach three times per day |
| Patient 4 | male | 52 | 393 | 160 | Drinking 200 [ml] of the beverage after getting up every morning |
| Patient 5 | male | 62 | 425 | 135 | Drinking 200 [ml] of the beverage after getting up every morning |

As shown in the above Table-1, it was demonstrated that the beverage has clinical significance for diabetes because the blood glucose levels of the patients 1-5 decreased after they drank it.

The patient 2 drank the beverage for another one week, resulting in the blood glucose level of the patient 2 decreasing to "130".

In addition, the beverage was mixed with an aloe containing cream by a ratio of 1:4, and the mixture was applied to palm, planta, and belly of the patient 3 at bedtime. Insulin secretion was observed in the patient 3 after one month, although the insulin had not been secreted until then. It was demonstrated that the beverage containing bamboo extract as the main ingredient of the present invention has clinical significance for diabetes because not only drinking it but also applying it causes the amelioration of diabetes.

Example-2

We prepared the beverage containing bamboo extract as the main ingredient of the present invention and examined the patients who had drunk it for the purpose of testing it. The examination was conducted by observing the patients' health status before and after drinking the beverage. The tested patients were cancer patients 6-9 (three males, one female, age range 51-67), asked to drink the beverage for two weeks. The patients each drank 200 [ml] of the beverage on an empty stomach three times per day.

Table-2 shows the patients' health status before drinking the beverage, their health status after two weeks of drinking it, and the condition of drinking it.

TABLE 2

| PATIENT | SEX | AGE | Health status of patients before drinking | Health status of patients after drinking | Condition of drinking the beverage |
|---|---|---|---|---|---|
| Patient 6 | male | 64 | Terminal stage of stomach cancer. Three months of life expectancy | Recovery to the extent to be able to have an operation after one month | Drinking 200 [ml] of the beverage on an empty stomach three times per day |
| Patient 7 | male | 67 | Colon cancer. Four months of life expectancy | Discharged from the hospital and recovery to the extent to be able to work on a farm after one month | Drinking 200 [ml] of the beverage on an empty stomach three times per day |
| Patient 8 | male | 65 | Liver cancer. One month of life expectancy | After two weeks, disappeared choloplania and discharged from the hospital | Drinking 200 [ml] of the beverage on an empty stomach three times per day |
| Patient 9 | female | 51 | Uterine cancer developed systemic metastasis | Suppression of cancer progression | Drinking 200 [ml] of the beverage on an empty stomach three times per day |

As shown in the above Table-2, the patients 6-8 recovered to the extent that they were able to have an operation and be discharged from the hospital, and cancer progression of the patient 9 was suppressed. As a result, it was demonstrated that the beverage containing bamboo extract as the main ingredient of the present invention has a clinical significance for cancer.

Example-3

We prepared the beverage containing bamboo extract as the main ingredient of the present invention and examined patients who had drunk it for the purpose of testing it. The examination was conducted by observing the patients' health status before and after drinking the beverage. The tested patients were patients with pollinosis (patients with allergy) 10-13 (two males, two female, age range 35-52), asked to drink the beverage from January before dispersal of Japanese cedar pollen. The patients drank 200 [ml] of the beverage after getting up every morning.

Table-3 shows the patients' health status before drinking the beverage (status of pollinosis developing every year), the patients' health status after drinking it from January (on the day of Japanese cedar pollen dispersing), and the condition of drinking it.

TABLE 3

| PATIENT | SEX | AGE | Status of patients before drinking the beverage | Status of patients after drinking the beverage | Condition of drinking the beverage |
|---|---|---|---|---|---|
| Patient 10 | male | 52 | severe rhinitis by pollinosis | Sometimes having a runny nose | Drinking 200 [ml] of the beverage after getting up every morning from January |
| Patient 11 | female | 35 | severe rhinitis by pollinosis | Recovery from rhinitis | Drinking 200 [ml] of the beverage after getting up every morning from January |
| Patient 12 | female | 44 | severe rhinitis by pollinosis | Blowing nose once in a while | Drinking 200 [ml] of the beverage after getting up every morning from January |
| Patient 13 | male | 42 | severe rhinitis by pollinosis | Recovery from rhinitis | Drinking 200 [ml] of the beverage after getting up every morning from January |

As shown in the above Table-3, it was demonstrated that the beverage containing bamboo extract as the main ingredient of the present invention has clinical significance for allergies like pollinosis because severe rhinitis in the patients 10-13 pestered with pollinosis every year were ameliorated after they drank it.

Furthermore, after the patient 11 applied the beverage to her eyes, itching of eye specific for the pollinosis was able to be prevented. As a result, it was demonstrated that the beverage has clinical significance for the allergies like pollinosis by not only drinking it but also applying it.

Example-4

We prepared the beverage containing bamboo extract as the main ingredient of the present invention and examined patients who had drunk it for the purpose of testing it. The examination was conducted by observing the patients' health status before and after drinking the beverage. The tested patients were patients 14-17 (four males, zero female, age range 53-56) with abnormality of hormone balance caused by climacteric disorder, asked to drink the beverage for two weeks. The patients drank 50-200 [ml] of the beverage after getting up every morning.

Table-4 shows the patients' health status before drinking the beverage, the patients' health status after drinking it, and the condition of drinking it.

TABLE 4

| PATIENT | SEX | AGE | Status of patients before use | Status of patients after use | Condition of use |
|---|---|---|---|---|---|
| Patient 14 | male | 55 | Not being able to move arm caused by frozen shoulder | Coming to be able to move arm | Drinking 50 [ml] of the beverage after getting up every morning |
| Patient 15 | male | 53 | Not being able to grip objects caused by peritendinitis | Coming to be able to grip objects | Drinking 100 [ml] of the beverage after getting up every morning |
| Patient 16 | male | 54 | Not being able to move arm and foot in pain | Able to move arm and foot, and in therapy now | Drinking 100 [ml] of the beverage after getting up every morning |
| Patient 17 | male | 56 | Having no hair | Sprouting thin hairs after two weeks | Drinking 200 [ml] of the beverage after getting up every morning |

As shown in the above Table-4, it was demonstrated that the beverage has clinical significance for abnormality of hormone balance like climacteric disorder because pains in the patients 14-17 pestered with the abnormality of hormone balance like climacteric disorder were ameliorated by drinking it.

Example-5

We prepared a medicament, which is the beverage containing bamboo extract as the main ingredient of the present invention containing 1% sodium hyaluronate, and examined patients who had applied it for the purpose of testing it. The examination was conducted by observing the patients' health status before and after applying the medicament. The tested patients were patients 18-21 with abnormality of hormone balance like climacteric disorder (four males, zero female, age range 55-64), asked to apply the medicament to the affected part for two weeks.

Table-5 shows the patients' health status before applying the medicament which is the beverage containing bamboo extract as the main ingredient of the present invention containing 1% sodium hyaluronate, the patients' health status after applying it, and the condition of use.

TABLE 5

| PATIENT | SEX | AGE | Status of patients before use | Status of patients after use | Condition of use |
|---|---|---|---|---|---|
| Patient 18 | male | 55 | Not being able to move arm caused by frozen shoulder | Able to move arm | Spraying the medicament on the affected part |
| Patient 19 | male | 56 | Not being able to move arm caused by frozen shoulder | Able to move arm | Spraying the medicament on the affected part |
| Patient 20 | male | 61 | Not being able to grip objects caused by peritendinitis | Able to grip objects | Spraying the medicament on the affected part |
| Patient 21 | male | 64 | Not being able to walk by pain of knee | The pain disappeared and foot felt light | Spraying the medicament on the affected part |

As shown in the above Table-5, it was demonstrated that the medicament which is the beverage containing bamboo extract as the main ingredient of the present invention containing 1% sodium hyaluronate has clinical significance for abnormality of hormone balance like climacteric disorder because pains in the patients pestered with the abnormality of hormone balance like climacteric disorder were ameliorated by spraying it on the affected part.

Example-6

We prepared the beverage containing bamboo extract as the main ingredient of the present invention and examined patients who had drunk it for the purpose of testing it. The examination was conducted by observing the patients' health status before and after drinking the beverage. The tested patients were patients suffering from constipation 22-25 (two males, two females, age range 35-72), asked to drink the beverage for one week. The patients drank 100 [ml] of the beverage.

Table-6 shows the patients' health status before drinking the beverage, the patients' health status after drinking it, and the condition of drinking it.

TABLE 6

| PATIENT | SEX | AGE | Status of patients before use | Status of patients after use | Condition of use |
|---|---|---|---|---|---|
| Patient 22 | male | 64 | Having a bowel movement every three days despite of taking cathartic | A bowel movement once a day | Drinking 100 [ml] of the beverage every morning and before bedtime |

TABLE 6-continued

| PATIENT | SEX | AGE | Status of patients before use | Status of patients after use | Condition of use |
|---|---|---|---|---|---|
| Patient 23 | male | 35 | Having a bowel movement every three days despite of taking cathartic | A bowel movement after breakfast | Drinking 100 [ml] of the beverage after getting up every morning |
| Patient 24 | female | 44 | Not having a bowel movement until taking cathartic and having an enema | A bowel movement after breakfast | Drinking 100 [ml] of the beverage after getting up every morning |
| Patient 25 | female | 72 | Having a bowel movement every three days despite of taking cathartic | A bowel movement on the next day | Drinking 100 [ml] of the beverage every morning and before bedtime |

As shown in the above Table-6, it was demonstrated that the beverage has clinical significance for constipation because constipation in the patients 22-25 ameliorated by drinking it.

Example-7

We prepared the beverage containing bamboo extract as the main ingredient of the present invention and examined patients who had applied it for the purpose of testing it. The examination was conducted by observing the patients' health status before and after applying the beverage. The tested patients were patients suffering from insomnia 26-29 (three males, one female, age range 39-49), asked to apply the beverage to the belly for one week before bedtime.

Table-7 shows the patients' health status before applying the beverage, the patients' health status after applying it, and the condition of applying it.

TABLE 7

| PATIENT | SEX | AGE | Status of patients before use | Status of patients after use | Condition of use |
|---|---|---|---|---|---|
| Patient 26 | male | 45 | Unable to sleep despite of taking hypnotic twice as much as optimum dose | Could sleep deeply without taking hypnotic until morning | Applying the beverage to the belly before bedtime |
| Patient 27 | male | 49 | Unable to sleep despite of taking hypnotic twice as much as optimum dose | Could sleep deeply without taking hypnotic until morning | Applying the beverage to the belly before bedtime |
| Patient 28 | female | 44 | Unable to sleep despite of taking hypnotic at optimum dose | Could sleep deeply without taking hypnotic until morning | Applying the beverage to the belly before bedtime |
| Patient 29 | male | 39 | Unable to sleep despite of taking hypnotic twice as much as optimum dose | Could sleep deeply without taking hypnotic until morning | Applying the beverage to the belly before bedtime |

As shown in the above Table-7, it was demonstrated that the beverage has clinical significance for insomnia because insomnia in the patients 26-29 ameliorated by applying it to the belly.

Example-8

We prepared the beverage containing bamboo extract as the main ingredient of the present invention and examined patients who had applied it for the purpose of testing it. The examination was conducted by observing the patients' health status before and after applying the beverage. The tested patients were patients pestered with wrinkles and chloasma 30-31 (zero male, two females, age range 66-70), asked to apply the beverage to the affected part.

Table-8 shows the patients' health status before applying the beverage, the patients' health status after applying it, and the condition of applying it.

TABLE 8

| PATIENT | SEX | AGE | Status of patients before use | Status of patients after use | Condition of use |
|---|---|---|---|---|---|
| Patient 30 | female | 66 | A lot of fine-wrinkles and chloasma in an entire body | After two months, chloasma were getting light, and the number of fine-wrinkles decreased | Applying the beverage to an entire body after taking a bath |
| Patient 31 | female | 70 | Concerning about chloasma in the face | After three months, chloasma were getting light | Applying the beverage to the face after taking a bath |

As shown in the above Table-8, it was demonstrated that the beverage has clinical significance for wrinkles and chloasma because wrinkles and chloasma in the patients 30-31 ameliorated by applying it to the affected part.

ADVANTAGEOUS EFFECT OF THE INVENTION

A beverage containing bamboo extract as the main ingredient of the present invention can ameliorate diseases such as diabetes, complications of diabetes, cancer, hepatic dysfunction, stiff shoulder, atopy, allergies, pollinosis, life-style related diseases, climacteric disorder, recovery from fatigue, recovery of vitality, rheumatism, neuralgia, insomnia, constipation, diarrhea, body odor, chloasma, freckle, wrinkles, dandruff, itch of tinea pedis, chapped skin, accelerating hair growth, frozen shoulder, and peritendinitis by drinking or applying it to the affected part. The present invention can heal and prevent life-style related diseases and the like, which has become a social problem.

INDUSTRIAL APPLICABILITY

The beverage containing bamboo extract as the main ingredient of the present invention can provide a beverage that is useful for treating diseases such as diabetes, complications of diabetes, cancer, hepatic dysfunction, stiff shoulder, atopy, allergies, pollinosis, life-style related diseases, climacteric disorder, recovery from fatigue, recovery of vitality, rheumatism, neuralgia, constipation, diarrhea, body odor, chloasma, freckle, wrinkles, dandruff, itch of tinea pedis, chapped skin, accelerating hair growth, frozen shoulder, peritendinitis or the like.

LIST OF REFERENCES

Patent Literature-1

Japanese Patent Application Laid-open No. 2003-289829 A

Patent Literature-2

Japanese Patent Application Laid-open No. 2004-8120 A

Although the best time to pick bamboo is between September and January to obtain bamboo extracts with the most hormones, minerals and vitamins, it is desirable to preserve the bamboo extracts for use through out the year.

In one exemplary embodiment, a bamboo extract may be obtained by following the steps shown in FIG. 1. First, bamboo may be cut and/or split into pieces and immersed in to water in a container (step 100).

Next the water and the bamboo pieces may be heated to, for example, a temperature between 95° C. to 101° C. for a period of, for example, between 2 hr 45 min to 3 hr 15 min (step 110). Preferably the temperature in step 110 does not reach above 101° C. because the protein tryptophan that is within the bamboo pieces has a melting point of 103° C.

The heated water with bamboo pieces may then be filtered (step 120) by, for example, pouring the heated water with bamboo pieces through a filter into another container. During the filtration in step 120, proteins containing tyrosine, lipids (i.e. horse oil, camellia oil or the like), and hormone saccharides (poly saccharides) are removed. Once the liquid is filtered, it may be cooled (step 130) to, for example, a temperature of 30° C. or less. The filtering and cooling of steps 120 and 130 allows the liquid to be preserved for about three years without substantially losing beneficial properties such as the protein tryptophan (that allows cells to lengthen), the hormone gibberellin (used to correct distortions in the cells) and the growth hormone cytokinin (like Interleukin-2, urges cell division).

When it is desired to use the stored liquid, the liquid is heated (step 140) to, for example, a temperature of between 85° C. to 101° C. This heating step allows the removal of microorganisms and the like from the stored liquid.

In an exemplary embodiment, the bamboo extract obtained in the above steps may be mixed with one or more other liquids (step 150). For example, the bamboo extract may be mixed with a beverage for drinking or may be mixed with a solid excipient or another liquid to be used as a medicament.

In another exemplary embodiment, in step 100, herbs may also be added to the water. If the bamboo extract in this embodiment is mixed with another liquid in step 150, the herbs may make up to 2% of the final mixture.

In another exemplary embodiment, in step 100, spices may be added to the water. If the bamboo extract in this embodiment is mixed with another liquid in step 150, the spices may make up to 10% of the final mixture.

In another exemplary embodiment, in step 100, spices and herbs may be added to the water of the container. If the bamboo extract in this embodiment is mixed with another liquid in step 150, the spices may make up to 10% of the final mixture and herbs may make up to 2% of the mixture.

In another exemplary embodiment, the bamboo extract may be mixed with a solid excipient or liquid to be used as a medicament in step 150, where the bamboo extract may make up 15% to 25% of the medicament and a sodium hyaluronate may make up 0.2% to 2.0% of the medicament.

In another exemplary embodiment, the bamboo extract having magnesium and zinc may be mixed with a solid excipient or liquid to be used as a medicament in step 150, where the medicament may be used to treat diabetes.

In another exemplary embodiment, in step 140, aloe and capsaicin may be added to the water after the water is heated. The resulting liquid may be used to restore hair.

In another exemplary embodiment, the bamboo extract having cytokinin acid and abscisic acid may be mixed with a solid excipient or liquid to be used as a medicament in step 150, where the medicament may be used to treat cancer.

The abscisic acid is a growth inhibitory hormone of the bamboo that may be used to treat cancer. As known, cancer cells will metastasize before the Interleukin-2 from the T4 cells they produce can have its beneficial effect. With the help of abscisic acid, the growth of the cancer cells maybe sufficiently inhibited to allow the production of the T4 cells that secrete Interleukin-1 and Interleukin-2 to help fight cancer.

The complement fixation (it is assumed that the cell membrane of the cancer cell can be melted, and the white blood corpuscle invade the cancer cell) becomes impossible as for the natural recovery mechanism of cancer due to secretion shortage of IgG of the immunoglobulin secreted from the plasma cell in B-lymphocyte, and the cancer cannot be spontaneously healed. Interleukin-1 and -2 are necessary for the immunoglobulin to be secreted enough from the plasma cell. Interleukin-1 is provided from macrophage. However, Interleukin-2 is secreted from T4 cell in T-lymphocyte (helper/inducer T-lymphocyte). The absence of T4 cell is a key factor.

This is similarly related to trichophystosis fungi (athlete's foot and the like) and the allergy in liquid immunity. Melting the cell membrane of the cancer cell enough only by the extracted material from the bamboo even if help such as hyaluronic acids is not gotten because the melting point is 105° C.-110° C., sending the cancer cell the white blood corpuscle, and demonstrating the ability to root out the cancer cell become possible though Interleukin-2 exists in Phyllostachys heterocycla extract as a kind of cytokinin.

In addition, it has not necessarily cured because cancer metastasizes if the function will not be recovered by the time the T4 cell is secreted. It is possible for the secretion of the T4 cell by the effect of rejuvenation of the cell of the reducing power of the abscisic acid that is the growth inhibitory hormone of the bamboo. Therefore, the medicament of the present disclosure enables treatment of cancer as for the complete cure of the metastasizing cancer.

The bamboo extract penetrates into the inside of the body by passing the skin and the hypodermic when spreading it on the skin because the interfacial revitalization action is strong.

The reason to use the hyaluronic acid for this invention with the oil such as the horse oil and camellia oil is used to stay for a long time between the skin and the hypodermic to make a prof i table bamboo hormone in the bamboo extract. Mainly, it uses it as a medicine for external application.

Only if Phyllostachys heterocycla is treatment with the temperature of only 100° C. or more, the material (especially ubiquinone derivatives in the part of the bamboo's skin) to expect only an antibiotical effect in the hormone is oils and fats group, and it is possible to extract it because the melting point is very high. But then, a long preservation of the liquid that is obtained by compressing and mixing with water is impossible, because the adhesion of the microorganism (especially, a kind of diatoms and blue mold and black mold) is early. In this invention, it is possible for cooling and a filtration process to remove the protein, the oils and fats, and the like. When only the antibiotic property is valued, it is impossible to maintain it without ruining the hormone as this inventive medicine though it is certainly effective for the extraction that we use ether, ethanol and the like to inhibit the adhesion of the microorganism.

The invention claimed is:

1. A method for manufacturing a liquid containing bamboo extract as a main ingredient, the method comprising:
   obtaining a bamboo extract; and
   mixing the bamboo extract with a liquid, wherein the liquid comprises aloe and capsaicin;
   wherein obtaining the bamboo extract comprises:
      immersing bamboo pieces in water in a first container;
      heating the water and the bamboo pieces in the first container to a temperature between 95° C. to 101° C.;
      maintaining the temperature in the first container between 95° C. to 101° C. for a period of 2 hr 45 min to 3 hr 15 min;
      pouring heated water in the first container into a second container through a filter;
      cooling the second container to a temperature of 30° C. or less; and
      heating the second container to a temperature between 85° C. to 101° C.

2. The method of claim 1, wherein obtaining the bamboo extract further comprises immersing herbs in the water in the first container before the water and the bamboo pieces in the first container are heated to the temperature between 95° C. to 101° C.

3. The method of claim 2, wherein the herbs make up 2% of the liquid mixed with the bamboo extract.

4. The method of claim 1, wherein obtaining the bamboo extract further comprises immersing spices in the water in the first container before the water and the bamboo pieces in the first container are heated to the temperature between 95° C. to 101° C.

5. The method of claim 4, wherein the spices make up 10% of the liquid mixed with the bamboo extract.

6. The method of claim 1, wherein obtaining the bamboo extract further comprises immersing herbs and spices in the water in the first container before the water and the bamboo pieces in the first container are heated to the temperature between 95° C. to 101° C.

7. The method of claim 6, wherein the spices make up 10% of the liquid mixed with the bamboo extract and the herbs make up 2% of the liquid mixed with the bamboo extract.

8. The method of claim 1, wherein the mixture of the bamboo extract and the liquid comprises sodium hyaluronate.

9. The method of claim 8, wherein the sodium hyaluronate makes up 0.2%-2.0% of the liquid mixed with the bamboo extract and the sodium hyaluronate.

10. The method of claim 9, wherein the bamboo extract makes up 15.0%-25.0% of the liquid mixed with the bamboo extract and the sodium hyaluronate.

11. The method of claim 8, wherein the liquid is a medicament.

12. The method of claim 1, wherein the mixture of the bamboo extract and the liquid comprises magnesium and zinc.

13. The method of claim 1, wherein the mixture of the bamboo extract and the liquid comprises cytokinin and abscisic acid.

* * * * *